United States Patent [19]
Baldini

[11] 4,161,504
[45] Jul. 17, 1979

[54] PROCESS OF MAKING A FILTER ELEMENT FOR USE IN INTRAVENOUS INFUSIONS

[75] Inventor: Luciano Baldini, Grosotto, Italy
[73] Assignee: Bieffe S.p.A., Grosotto, Italy
[21] Appl. No.: 782,054
[22] Filed: Mar. 28, 1977
[30] Foreign Application Priority Data
Aug. 10, 1976 [IT] Italy .................... 26186 A/76
[51] Int. Cl.² .................... B29D 23/02
[52] U.S. Cl. .................... 264/163; 264/252; 264/257; 264/273
[58] Field of Search .......... 264/163, 257, 273, 252, 264/250, 266

[56] References Cited
U.S. PATENT DOCUMENTS

| | | | |
|---|---|---|---|
| 1,482,045 | 1/1924 | Stearns | 264/266 X |
| 3,077,658 | 2/1963 | Wharton | 264/266 X |
| 3,107,991 | 10/1963 | Taussig | 264/257 X |
| 3,408,438 | 10/1968 | Staunton | 264/257 X |
| 3,653,098 | 4/1972 | Lagarde | 264/273 X |
| 3,890,679 | 6/1975 | Simon | 264/252 X |

*Primary Examiner*—Thomas P. Pavelko
*Attorney, Agent, or Firm*—Young & Thompson

[57] ABSTRACT

A process for making a filter element for use in intravenous infusions, comprises positioning a filter fabric between two half molds and then injecting plastic material into the two half molds to provide a tubular filter element transected by the filter fabric. In order to promote bonding between the fabric and the plastic, and thereby to avoid the formation of a transverse plane of weakness in the filter element coincident with the plane of the fabric, the half molds are provided with spaced cutting means in the form of knives arranged in a peripheral series about the mold in such position as to penetrate the fabric at a plurality of spaced points when the mold is closed with the fabric between the mold halves.

1 Claim, 5 Drawing Figures

U.S. Patent      Jul. 17, 1979      4,161,504
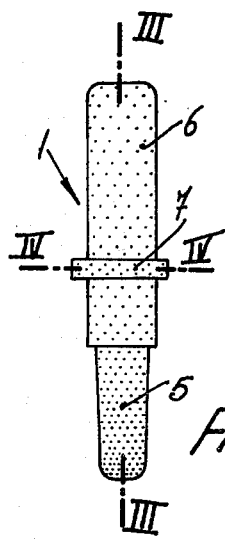
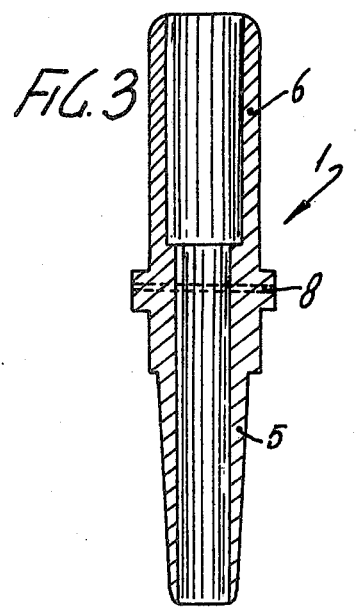
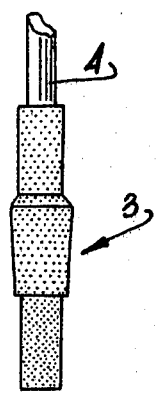
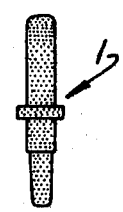
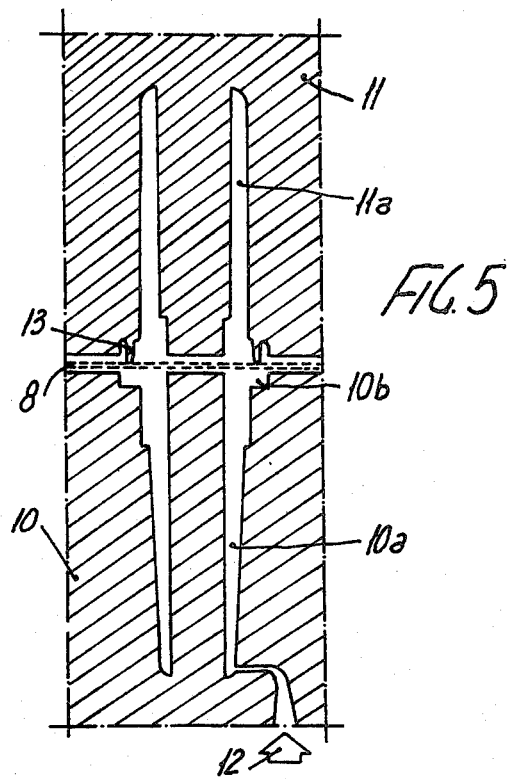

PROCESS OF MAKING A FILTER ELEMENT FOR USE IN INTRAVENOUS INFUSIONS

This invention relates to a process for making a filtering device to be applied to tubular apparatus of plastics as used for solution intravenous infusion, such a filter being positioned as close as possible to the vein, so that both the impurities from the infused solution and those within the defluxer are retained.

Filters have already been known, such as those made of sintered steel, but these filters are extremely expensive both because of the material used and because of the necessary processing of the same.

It is the object of the present invention to provide a method of making an infusion filter which is extremely inexpensive, of easy construction, and having such a filtering capacity that all of those particles that could occlude the capillary vessels are retained.

According to the present invention, the above specified objects have been accomplished by providing that a filtering unit of plastics is so molded as to comprise in its interior a fabric of a very fine weft, which will constitute the actual filter. A fabric having a stitch opening of 7 microns was used, since the finest capillary vessels are of such a diameter.

A molding process according to the present invention provides that the die or mold is divided into two halves, a fabric of nylon or the like is included or inserted therebetween, the material forming the plastic unit of the filter is caused to pass both through the fabric holes and through apertures formed in said fabric by knives included in at least one of said two half dies or molds, and then the fabric is sheared at the outside periphery of the filtering units.

The invention will now be described in futher detail with reference to the exemplary embodiment shown in the accompanying drawing, in which:

FIG. 1 is an exploded view showing an infusion device;

FIG. 2 is an enlarged side view showing the filtering unit comprising the fabric according to the present invention;

FIG. 3 is an axial sectional view of the filtering unit shown in FIG. 1;

FIG. 4 is an enlarged sectional view taken along line IV—IV of FIG. 2; and

FIG. 5 is a sectional view showing a detail of the die or mold for providing the filtering unit according to FIG. 2.

First referring to FIG. 1, it will be seen that an infusion device comprises a filtering unit 1, a needle 2, and a sleeve 3 for connecting said filtering unit with a tube 4 of polyvinyl chloride admitting the infusion liquid, said sleeve 3 being made of para rubber.

Referring to FIGS. 2 through 4, the filtering unit 1 will now be described. This filtering unit comprises two tubular end portions 5 and 6 and a somewhat central portion 7 of a largest section, having included or inserted therein the fabric, the latter being selected with very thick weft and warp, so that the maximum side of each hole is extremely reduced. Particularly, use is made of a fabric of nylon 6.6, the maximum side of the hole of which is 7 microns. Obviously, other fabrics can be used, but generally it is desirable to use fabrics of the highest strength having a maximum passage side which is extremely reduced.

The filtering supporting unit holding the fabric in its interior is generally molded of polythene, but other similar plastic materials can be also used. In the sectional view of FIG. 4, it will be seen that the inner zone, designated at 8a, is the zone for carrying out the filtering operation. Apertures 9 are provided in the fabric at the outer zone of circular sector shape 8b, the apertures allowing the passage of polythene between the upper and lower portions or sides and imparting an enhanced strength to the unit, which otherwise would be weak and easy to break at the fabric zone, since the connection between the lower and upper tubular end portions 5 and 6, respectively, would otherwise occur only through the fabric holes.

A process according to the present invention for making the filter will now be described with reference to FIG. 5. The die or mold being used is that partially shown in FIG. 5, wherein a lower half die 10 and an upper half die 11 can be seen, these half dies having been cut away along the axis of the filtering unit. The admission of polythene or the like is accomplished from the location indicated by arrow 12, so that the material penetrates the hollow tubular lower portion 10a having such a shape as to make up the portion 5 shown in FIG. 3. In proximity to fabric 8, the hollow or cavity in said half die 10 widens out to provide an annular cavity 10b, at which the polythene will arrive and attempt to pass through the fabric holes. Elongated or punctiform cutting means or knives 13 are also provided. For the sake of greater clarity, the contact surface between half die 10 and half die 11 has been shown as slightly separated or spaced apart. Obviously, these two surfaces will be instead closely in contact with each other and will be separated or spaced apart only by the distance required for accomodating said fabric 8 therebetween. The cutting means or knives 13 penetrate just below fabric 8, tearing the latter at a series of peripherally spaced points at which the fabric is unsupported, as seen in FIG. 5, thereby allowing a more substantial flow of polythene through said fabric 8.

The upper half die or mold 11 is provided with annular cavities 11a, such as to make up the upper outer portion 6 of the above mentioned filtering unit.

Of course, said filtering unit 1 can have shapes other than that shown, provided that it comprises a fabric 8 for filtering the infusion liquid.

What is claimed is:

1. A process for making a filter which comprises an upper tubular portion and a lower tubular portion with filter fabric disposed in an intermediate enlargement, comprising providing two half molds each of which is so shaped internally as to produce one of said tubular portions, providing a plurality of cutting means projecting into the interior of a said half mold at a series of peripherally spaced points, positioning filter fabric between said two half molds, closing said two half molds together so that said cutting means penetrate and tear said fabric at said plurality of spaced points with said fabric unsupported at said plurality of spaced points, and then injecting plastic material into one of said two half molds and about said cutting means so that said plastic flows on both sides of said fabric, the tearing of the fabric allowing a more substantial flow of plastic through the fabric thereby to promote an improved bond between the plastic and the fabric.

* * * * *